(12) United States Patent
Huelskamp et al.

(10) Patent No.: US 8,060,204 B2
(45) Date of Patent: Nov. 15, 2011

(54) LOW POWER DIGITAL DESIGN FOR DEEP SUBMICRON TECHNOLOGY

(75) Inventors: Paul Huelskamp, St. Paul, MN (US); Douglas J. Gifford, Ham Lake, MN (US); Scott A. Reedstrom, Vadnais Heights, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 202 days.

(21) Appl. No.: 12/394,693

(22) Filed: Feb. 27, 2009

(65) Prior Publication Data

US 2009/0222055 A1 Sep. 3, 2009

Related U.S. Application Data

(60) Provisional application No. 61/032,383, filed on Feb. 28, 2008.

(51) Int. Cl.
*A61N 1/00* (2006.01)

(52) U.S. Cl. .......................................... 607/27

(58) Field of Classification Search ................ 607/16, 607/27; 326/14
See application file for complete search history.

(56) References Cited

U.S. PATENT DOCUMENTS

| | | | |
|---|---|---|---|
| 5,350,407 A * | 9/1994 | McClure et al. ............... | 607/16 |
| 5,354,319 A | 10/1994 | Wyborny et al. | |
| 5,411,536 A | 5/1995 | Armstrong | |
| 5,607,458 A | 3/1997 | Causey, III et al. | |
| 5,792,201 A | 8/1998 | Causey, III et al. | |
| 6,128,528 A | 10/2000 | Erickson et al. | |
| 6,167,303 A | 12/2000 | Thompson | |
| 6,185,454 B1 | 2/2001 | Thompson | |
| 6,230,058 B1 | 5/2001 | Legay | |
| 6,456,875 B1 | 9/2002 | Wilkinson et al. | |
| 6,532,389 B1 | 3/2003 | Shahandeh | |
| 7,027,872 B2 | 4/2006 | Thompson | |
| 7,228,182 B2 | 6/2007 | Healy et al. | |
| 2005/0216063 A1 | 9/2005 | Hoyme et al. | |
| 2006/0247708 A1 | 11/2006 | Yost et al. | |
| 2007/0208261 A1 | 9/2007 | Maniak et al. | |
| 2008/0238472 A1* | 10/2008 | Simmons .................... | 326/14 |

* cited by examiner

*Primary Examiner* — George Manuel
*Assistant Examiner* — Robert Wieland
(74) *Attorney, Agent, or Firm* — Schwgman, Lundberg & Woessner, P.A.

(57) ABSTRACT

An apparatus comprises an implantable medical device that includes a storage circuit. The storage circuit includes a first stage circuit configured to receive an input signal and to invert and store information about a data bit received in the input signal, a second stage circuit coupled to the output of the first stage circuit to invert and store information about a data bit received from the first stage circuit, and an error circuit coupled to the output of the first stage circuit and an output of the second stage circuit. The error circuit generates an error indication when the storage circuit outputs match while the first stage circuit and the second stage circuit are in an inactive state.

19 Claims, 7 Drawing Sheets

LOW POWER DIGITAL DESIGN FOR DEEP SUBMICRON TECHNOLOGY

RELATED APPLICATIONS

This application claims the benefit under 35 U.S.C. 119(e) of U.S. Provisional Patent Application Ser. No. 61/032,383, filed on Feb. 28, 2008, which is incorporated herein by reference in it entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

IMDs typically have an electronics unit that includes one or more integrated circuits (ICs) designed to perform a variety of functions, such as timing or to provide therapy. The minimum size of transistors in the ICs continues to be reduced as technology advances. This miniaturization trend continues to allow more and more transistors to be placed on a die. This additional circuitry has in turn provided an increase in circuit performance, and allowed an increased number of device features and therapies to be included in the IMDs. In the past, as transistor device feature sizes decreased, the main concern of IMD design was to put more functionality in an IC and less concern was given to altering design techniques to accommodate the reduced feature size.

OVERVIEW

This document relates generally to devices and methods that provide cardiac function management to a patient or subject. In example 1, an apparatus includes an implantable medical device having a storage circuit. The storage circuit includes a first stage circuit configured to receive an input signal and to invert and store a data bit received in the input signal, a second stage circuit coupled to an output of the first stage circuit to invert and store a data bit received from the first stage circuit, and an error circuit coupled to the output of the first stage circuit and an output of the second stage circuit. The error circuit is configured to generate an error indication when the storage circuit outputs provide matching data bits while the first stage circuit and the second stage circuit are in an inactive state.

In example 2, the storage circuit of example 1 optionally includes a clock circuit configured to receive a global clock signal and an off signal, and to provide a local clock signal to the first stage and second stage circuits. The local clock signal is disabled when the off signal is received. The first stage circuit includes a first latch circuit having cross coupled logic gates configured to invert and store a data bit received in the input signal, the second stage circuit includes a second latch circuit having cross coupled logic gates configured to invert and store the data bit received from the first latch circuit, and the error circuit is configured to generate an error indication when the outputs match while the off signal is active.

In example 3, the second stage circuit of one or more of examples 1 and 2 is configured to store data on an opposite level of the global clock signal from the first stage circuit. In example 4, the implantable medical device of one or more of examples 1-3 optionally includes a plurality of storage circuits associated with respective error circuits. The error circuits are serially connected to form an error indication chain.

In example 5, the storage circuit of one or more of examples 1-4 optionally includes a first transistor having a voltage threshold lower than the voltage threshold of a second transistor of the storage circuit. In example 6, the first transistor of one or more of examples 1-5 is optionally included in a signal path that is more time sensitive than a signal path including the second transistor.

In example 7, the implantable medical device of one or more of examples 1-6 optionally includes a logic gate circuit including a stack of three series connected transistors. The three series connected transistors includes a first transistor having a voltage threshold that is lower than a voltage threshold of at least one of the other two transistors in the stack, and a gate of the first transistor is configured to receive an off signal to place the first transistor, the first stage storage circuit, and the second stage storage circuit in an inactive state.

In example 8, the implantable medical device of one or more of examples 1-7 optionally includes a redundancy circuit having a first, second, and third logic circuits, and a voting circuit. The second and third logic circuits are redundant instantiations of the first logic circuit. The voting circuit is configured to determine an output of the redundancy circuit according to a majority of outputs of the first, second, and third logic circuits.

In example 9, the storage circuit of one or more of examples 1-8 optionally includes a first transistor that is wider than a second transistor of the storage circuit. In example 10, the implantable medical device of one or more of examples 1-9 optionally comprises a cardiac function management device. In example 11, the implantable medical device of one or more of examples 1-10 optionally comprises at least one of a neural stimulation device, a drug delivery device, or a diagnostic device.

In example 12, a method includes storing, in a storage circuit of an implantable medical device, information to represent both an inverted version of a data bit and a non-inverted version of the data bit, disabling clocking of the storage circuit, and generating an error indication when the stored information to represent the inverted and non-inverted versions of the data bit match while the clocking is disabled.

In example 13, the method of example 12 optionally includes identifying a time sensitive signal path in the implantable device, wherein the time sensitive path includes the storage circuit, and providing a first transistor having a voltage threshold that is lower than a voltage threshold of a second transistor. The first transistor is included in the time critical signal path of the storage circuit.

In example 14, the methods of one or more of examples 12 and 13 optionally include incorporating a logic gate circuit in the electronic circuits. The logic gate circuit includes providing a logic gate circuit that includes three series connected transistors including a first transistor having a voltage threshold lower than the voltage threshold of at least one of the other two transistors in the stack. The first transistor is disabled when disabling the clocking of the storage circuit.

In example 15, the methods of one or more of examples 12-14 optionally include generating first, second, and third logic outputs. The second and third logic outputs are generated using logic that is redundant to logic used to generate the first and second logic outputs. The examples further include voting using the first, second, and third logic outputs to determine a majority output.

In example 16, the methods of one or more of examples 12-15 optionally include providing a clock signal to the storage circuit, and storing information to represent the inverted version of the data bit on an opposite level of the clock signal than the information to represent the non-inverted version of data bit.

In example 17, the methods of one or more of examples 12-16 optionally include providing a plurality of the storage circuits in association with respective error circuits, serially connecting the error circuits of the storage circuits into an error chain, and propagating an error indication to an output of the error chain when an error occurs in any of the storage circuits during disabling of the clocking of the storage circuits.

In example 18, the methods of one or more of examples 12-17 optionally include rewriting a register that includes a plurality of the storage circuits when an error indication is generated.

In example 19, the methods of examples 12-18 optionally include using the error indication to detect a disruption to operation of a cardiac function management device. In example 20, the methods of examples 12-19 optionally include using the error indication to detect a disruption to operation of at least one of a neural stimulation device, a drug delivery device, or a diagnostic device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
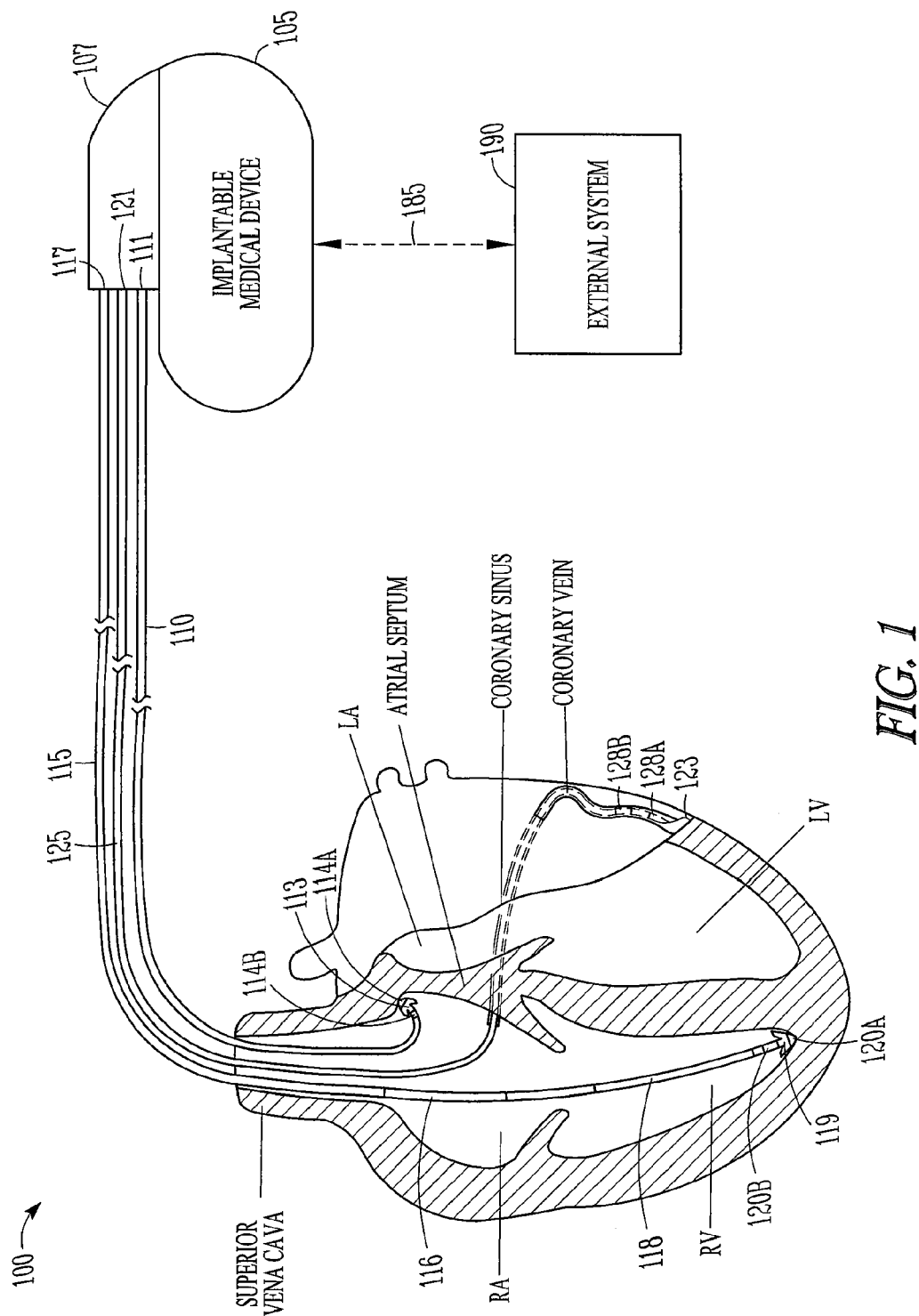
FIG. 1 is an illustration of portions of an example of a system that uses an EMD.

FIG. 1 is an illustration of an example of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As discussed previously, the minimum transistor size in ICs can be reduced as technology advances. Previous reductions in transistors sizes (e.g., from less than one micron to 500 nanometers (mn) to 250 nm to 180 nm, sometimes referred to as submicron technology) allowed IMD designers to focus mainly on putting more functionality in an IC. The present inventors have recognized that the subsequent technology reductions (e.g., to 130 nm or 90 nm, sometimes referred to as deep submicron technology), will present different and particularly difficult challenges that may have significant impact on IMD designs.

The present inventors have recognized that one of the particularly difficult challenges faced in using deep submicron technology is that using smaller geometry devices in electronic circuits of the IMD increases the likelihood of a disruption (e.g., a soft error) to the operation of the circuits. Soft errors may be caused by a charged particle striking a semiconductor memory or memory-type element (e.g., flip-flop or latch). A charge generated by the interaction of the incident particle and atoms of the semiconductor (e.g., in the form of electron-hole pairs) may corrupt information stored in the memory or memory-type element.

Memory (e.g., RAM) can be a primary area of concern for such disruptions and is typically the focus of error detection and correction. Examples of systems and methods to detect and correct single event upsets (SEUs) in memory are described in Hoyme et al., U.S. Patent Publication No. 20050216063, titled "System and Method for Recovery from Memory Errors in Medical Device" which is incorporated herein by reference in its entirety. The present inventors have recognized that with smaller transistor technology sizes, the ability of an incident particle to alter memory-type sequential logic of an DAD design increases. The present inventors have recognized that additional error detection in IMDs is useful in finding and in some cases resolving the disruptions.

Figure 2:
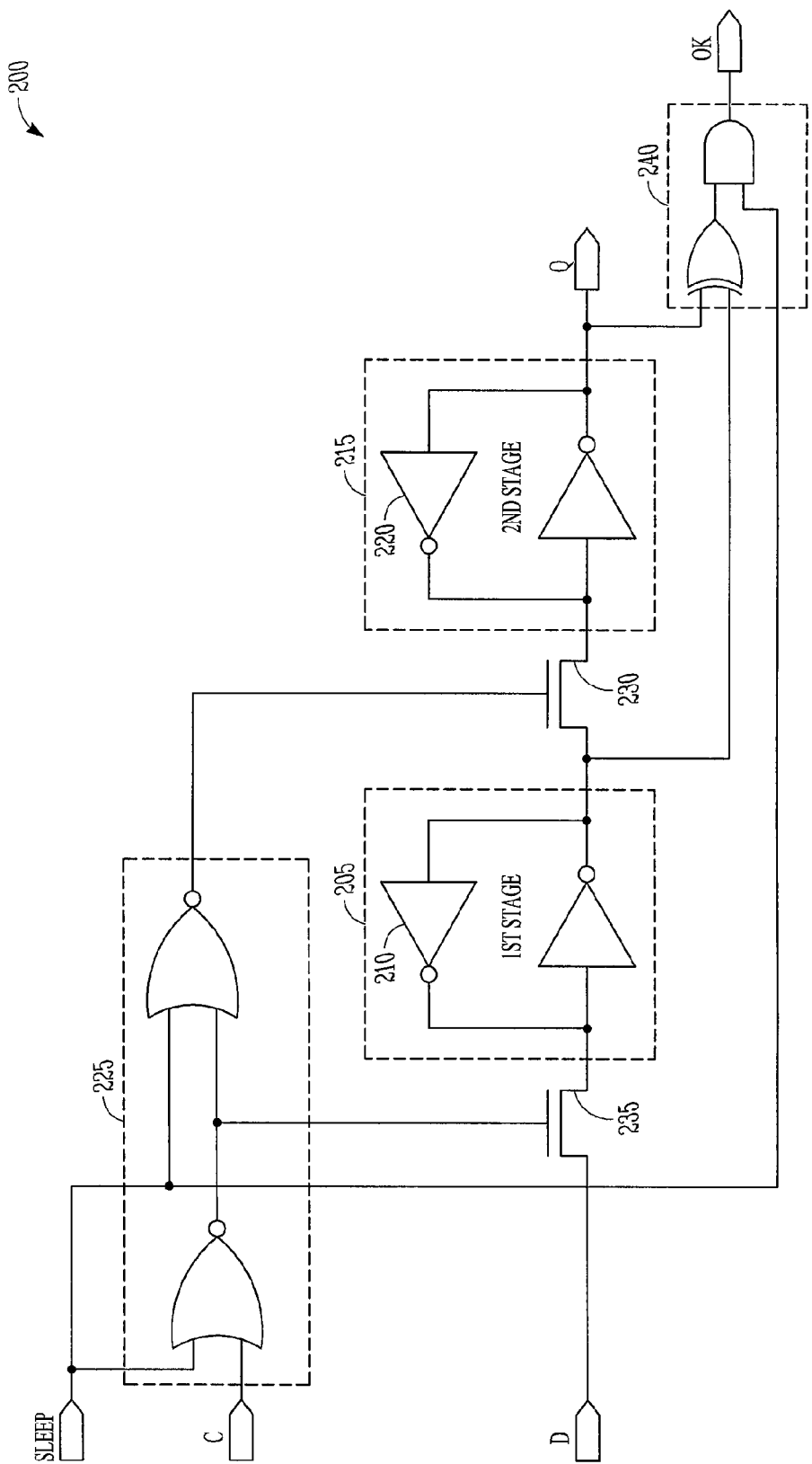
FIG. 2 is a schematic of an example of a storage circuit that is able to detect faults for use in sequential logic.

FIG. 2 is a schematic of an example of a storage circuit 200 (e.g., a flip-flop) that is able to detect faults and that is suitable for use in sequential logic, such as in an IMD. The storage circuit 200 includes two storage elements that respectively hold both the data and inverted data. The first stage circuit 205 receives an input signal on the "D" input and includes a first latch circuit having cross-coupled logic gates 210 to invert and store a data bit received in the input signal. Thus, the first latch circuit is configured to store the inverted data.

The second stage circuit 215 is coupled to the output of the first stage circuit 205. The second stage circuit 215 includes a second latch circuit having cross-coupled logic gates 220 to invert and store the data bit received from the first latch circuit. Thus the second latch circuit is configured to store the data.

The storage circuit 200 includes a clock circuit 225 configured to receive a global clock signal at the "C" input and provide a local clock signal to the first stage circuit 205 and the second stage circuit 215. In the example, the first stage circuit 205 includes a switch 235 configured to sample the signal at the D input while the global clock is low, and the second stage circuit 215 includes a switch 230 configured to sample the output of the first stage circuit 205 when the global clock is high. Thus, the second stage circuit 215 is configured to store data on an opposite clock level than the first stage storage circuit.

By adding a "sleep" (or halt, idle, stop, off, etc.) port to the storage circuit to disable clocking, the storage circuit can detect when the data in the first and second stages have the same logic level; thereby detecting a disruption (i.e., the storage circuit 200 is not storing data and inverted data).

To detect that the data stored in the first and second stages includes an error, the storage circuit 200 includes an error circuit 240 coupled to the output of the first stage circuit 205 and the output of the second stage circuit 215. The error circuit 240 generates an error indication (e.g., a low level signal at the "OK" output) when the storage circuit outputs match while the first stage circuit and the second stage circuit are in an inactive state (e.g., while the sleep or off signal is active and the clock circuit 225 is disabled). The "sleep" signal can be allowed to change only when the clock is off (e.g., high) to avoid false error detections. Note that the storage circuit cell can be larger with the error detection capability due to routing two additional signals.

Figure 3:
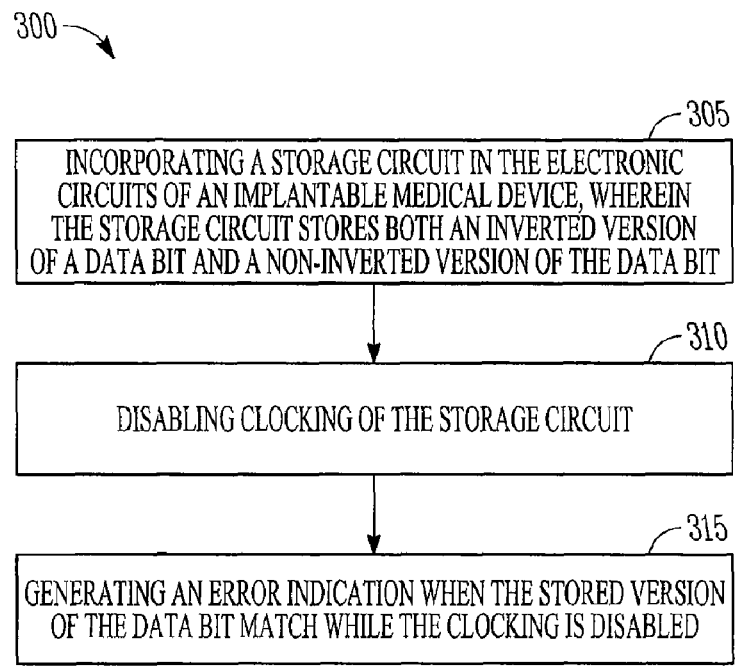
FIG. 3 shows a flow diagram of an example of a method of detecting disruptions in sequential logic of an EMD.

FIG. 3 shows a flow diagram of an example of a method 300 of detecting disruptions in sequential logic of an IMD. At block 305, a storage circuit is incorporated in the electronic circuits of an implantable medical device. The storage circuit stores both an inverted version of a data bit and a non-inverted version of the data bit. At block 310, clocking of the storage circuit is disabled. At block 315, an error indication is generated when the stored versions of the data bit match while the clocking is disabled.

Returning to FIG. 2, sequential logic of an IMD can include a plurality of the storage circuits 200 each having an error circuit 240. The output of the error circuits 240 can all be OR'ed together to indicate that a disruption occurred somewhere in the logic circuits. In another arrangement, the outputs of the error circuits 240 can be connected serially (e.g., a daisy chain) to form an error indication chain. In such an example, an error from any of the storage circuits propagates down the error chain to provide the error indication. For example, a plurality of the storage circuits 200 can be incorporated into a static register. The error circuits 240 of the static register can be daisy chained to provide an error indication when one or more of the storage circuits 200 includes an error. The register can be rewritten when an error indication is generated.

In some examples, the storage circuit 200 can be designed using wider transistors in order to be more resilient to disruptions from incident particles. In certain examples, the storage circuit 200 can be made more robust by using wider transistors in the latch circuit.

Other methods can be used to detect disruptions in the IMD. In some examples, the IMD includes parity checking and/or hamming codes to detect errors in sequential logic circuits that include finite state machines or counters. In certain examples, parity checking and/or hamming codes are used to detect errors in static registers. Dynamic updating can be used to rewrite a register when an error is indicated by the parity checking or hamming codes.

Typically, some sequential logic circuits provide more critical device operations than others. For example, the IMD can be a CFM device and can revert to operating in a safe mode (e.g., the NASPE/BPEG defined VOO mode of pacing) when one or more errors are detected. The IMD can operate in the safe mode by executing instructions from read only memory (ROM) or by progressing through device states in a finite state machine. To detect errors, redundant logic can be used in the circuits to detect failures. In certain examples, an error is declared to be detected when the logic states of two copies of the logic circuit do not match. To maintain operation in the presence of one or more errors, triple redundant logic can be used. Triple redundant logic allows voting to determine a majority outcome of the logic circuits. Using an odd number of logic circuits in the voting eliminates ties from occurring.

Figure 4:
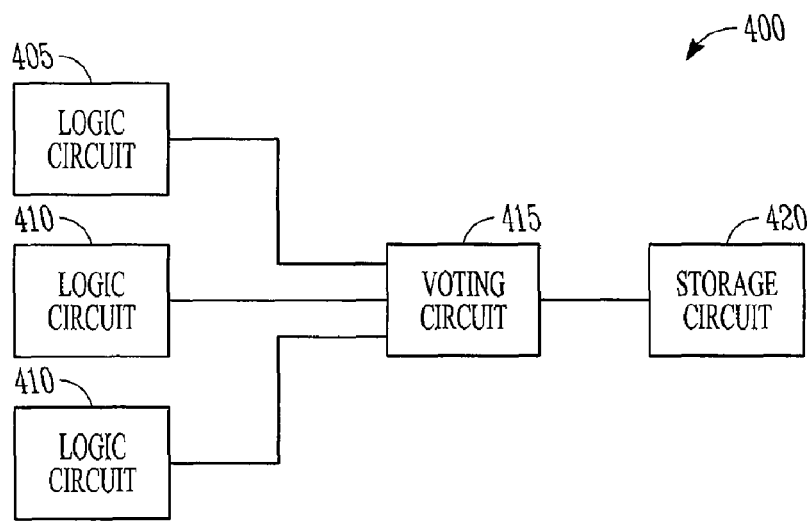
FIG. 4 shows an example of a redundancy circuit.

FIG. 4 shows an example of a redundancy circuit 400 that can be included in sequential logic of an IMD. The redundancy circuit 400 includes a first logic circuit 405, and second and third logic circuits 410 which are redundant copies of the first logic circuit 405. A voting circuit 415 determines the output of the redundancy circuit 400 according to a majority of outputs of the first, second, and third logic circuits. The majority outcome can then be captured in a storage circuit 420.

The present inventors have also recognized that another challenge in using smaller geometry devices is increased static current drain. Static current drain is due to leakage currents from reversed biased PN junctions associated with the source and drain of field-effect transistors, as well as transistor sub-threshold conduction currents. The leakage component is related to device areas and temperature. The sub-threshold component of leakage current is strongly dependent (and possibly exponentially dependent) on device threshold voltages. Sub-threshold leakage current becomes an important factor in static current drain when power supply voltage scaling is used to lower power by reducing the power supply voltage.

Figure 5:
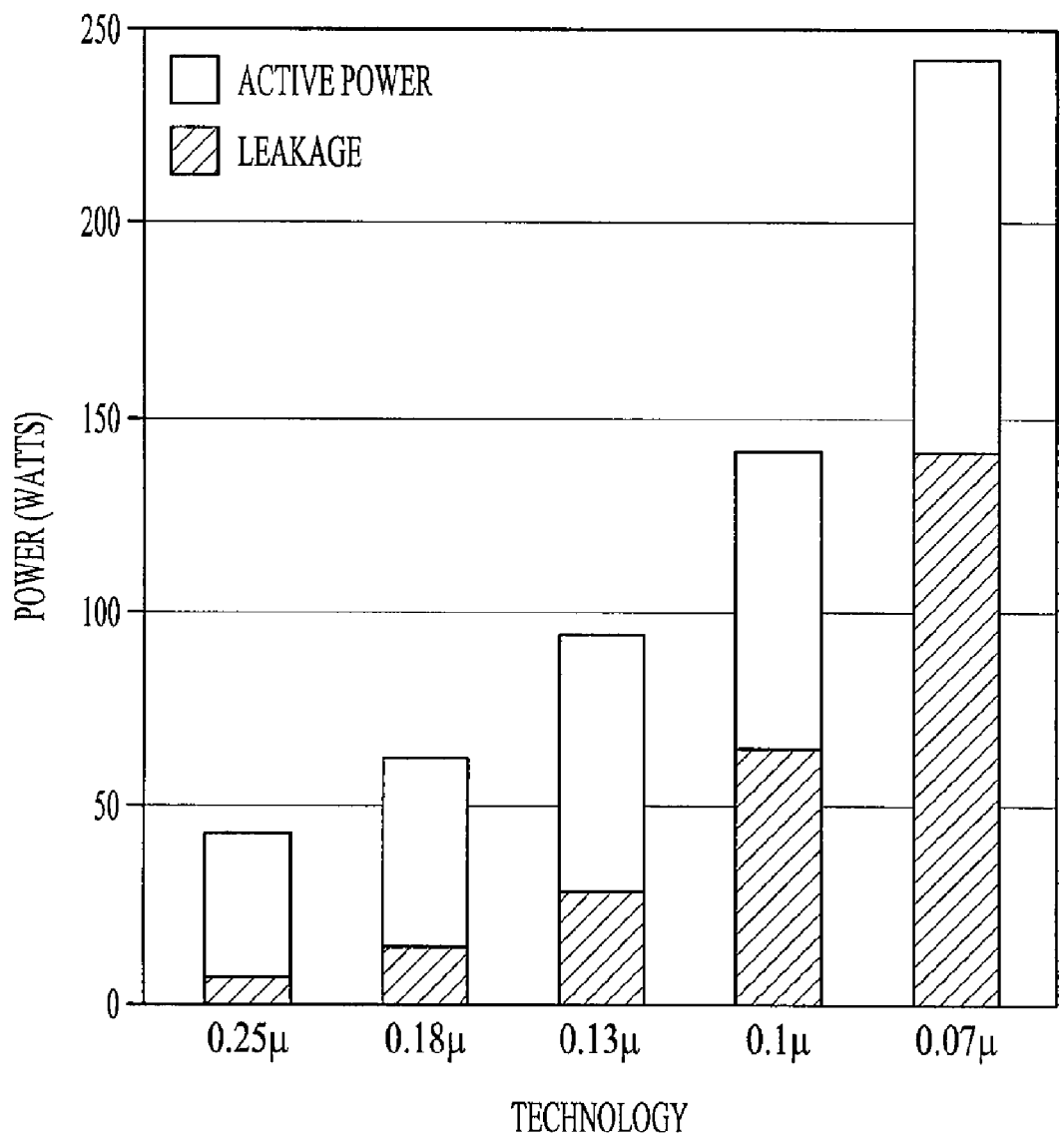
FIG. 5 shows an illustrative example of a graph of the scaling associated with threshold voltage and device size.

For systems with high ratio of standby operation to active operation, power drain due to leakage current ($P_{leakage}$) may be the dominant factor in determining overall battery life of the IMD. FIG. 5 shows an illustrative example of a graph of the scaling associated with threshold voltage and device size.

In addition, the present inventors have recognized that as the transistor sizes shrink variation in the leakage current increases dramatically. Although some advanced electronic design automation (EDA) tools may be able to account for and optimize the performance (speed) of each gate and associated load for a given supply operation, the leakage current in such tools is neither accounted for nor optimized. This is because leakage current is generally very process dependent and even local matching from one transistor to another is difficult Therefore, different transistors could have different levels of leakage even if they perform same exact function. In addition, transistor function can change from gate to gate. The individual effect of a particular transistor on the leakage current at the IC-level can widely vary. Leakage current is very difficult to quantify or predict at the block and IC-level and wide current distributions can exist.

The present inventors have recognized that, in some examples, the electronic circuit of an IMD can use a multiple voltage threshold ($V_T$) design, such as for example a dual voltage threshold ($V_T$) design, to reduce static current drain. High-$V_T$ transistors can be used to minimize or reduce leakage power without impacting circuit operating frequency. Performance critical transistors can be made low-$V_T$ to provide the required performance. For example, the storage circuit 200 of FIG. 2 can include a first transistor having a voltage threshold that is lower than the voltage threshold of a second transistor. The first transistor may be included in a signal path that is more time sensitive than a signal path that includes the second transistor. A time sensitive or time critical path includes a signal path that is more sensitive to a race condition than another signal path, and may be identified by one or more EDA tools.

A tailored dual-$V_T$ design can provide the same operating frequency as a design with single low-$V_T$, while limiting low-$V_T$ usage to 30%. As a result, leakage power during active and sleep can be reduced by an estimated 3× without any performance impact. Of course, process complexity is slightly higher since extra masking steps can be used to provide additional transistor $V_T$'s. EDA tools for tailored $V_T$ allocation during all phases of the design flow can help implement successful dual-$V_T$ designs. $V_T$ allocations can be performed at logic gate level or transistor level. While transistor level allocation can be effective for leakage power reduction, it also can be complex.

Another way to reduce static current drain is to design one or more combinational logic circuits to reduce leakage current. For example, the present inventors have recognized that leakage current through a stack of two or more "off" transistors can be an order of magnitude smaller than a single device leakage. This so-called "stack effect" becomes stronger with technology scaling downward to smaller transistor channel length dimensions. One approach can include adding a low threshold gate to the combinational elements. The low threshold gate device gets turned off in a "sleep" mode.

Figure 6:
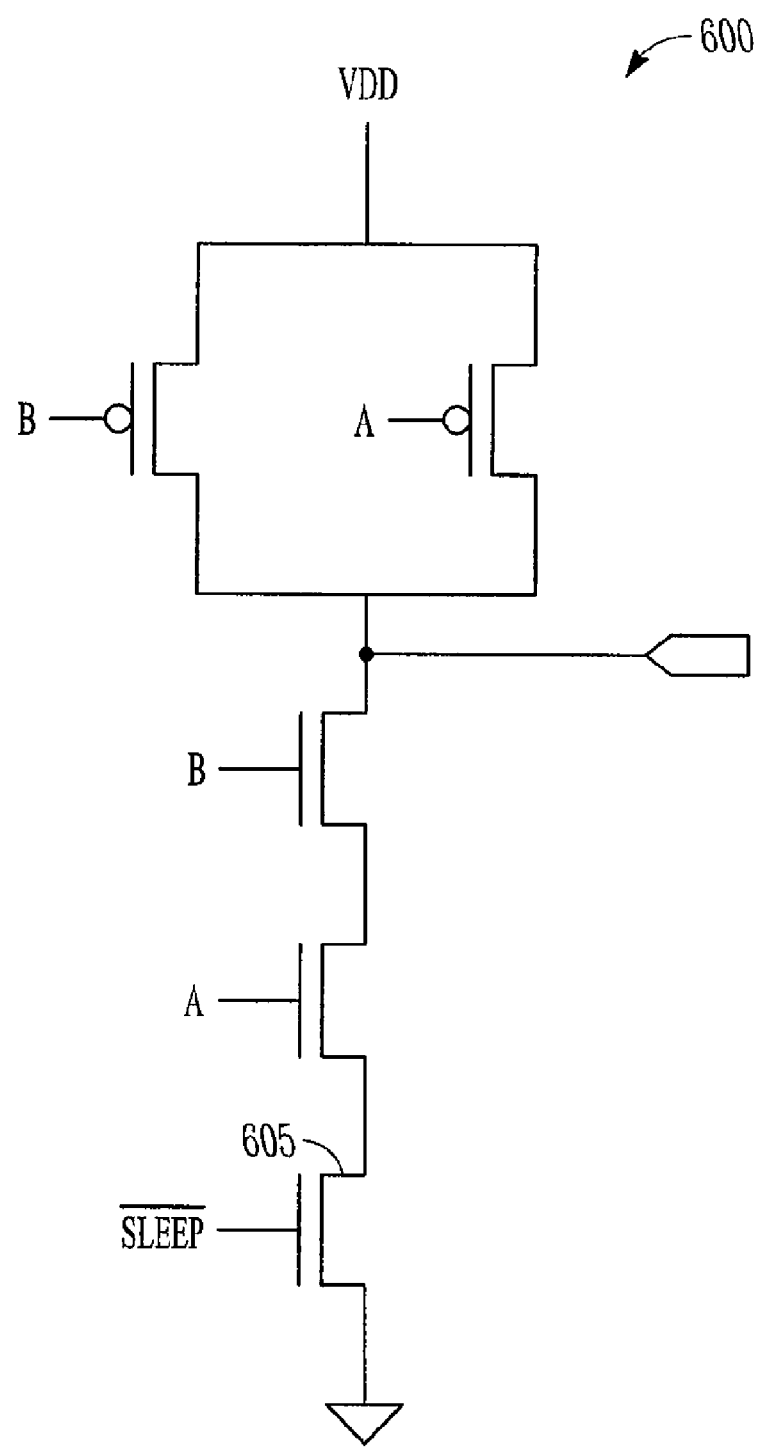
FIG. 6 is a schematic of an example of a logic gate circuit having a transistor stack.

FIG. 6 is a schematic of an example of a logic gate circuit 600 including a stack of three transistors. In this example, the stack of three transistors includes a first transistor 605 having a voltage threshold ($V_T$) that is lower than the voltage threshold of the other two transistors 610 in the stack. The gate of the first transistor 605 can be communicatively coupled to an off (or sleep) signal to turn off the first transistor.

The "sleep" signal that puts the combinational logic into a low leakage mode can be the same type of signal that places the first stage circuit and the second stage circuit of FIG. 2 in the inactive state. Therefore, an inactive state used to place portions of the electronic circuits of an IMD in a low power state can also be used to detect one or more disruptions while in the low power state.

The present inventors have recognized that this can be expanded to add a sleep signal to stacks of series-connected transistors in complex logic gates. By applying a sleep mode input vector to the combinational logic to place one or more gates in a reduced or minimum leakage mode, a significant reduction in leakage current can be achieved with minimal impact on area and performance.

The present inventors have also recognized that yet another way to reduce static current drain is to incorporate multiple voltage supply "islands" in an IC of the IMD. Multiple voltage islands can be used to support different digital supply voltages on the same IC. Combining the use of multiple voltage islands with automatically shifting of voltage supply levels to manage power consumption, allows a multiple power management opportunities for an EMD. In some examples, a microprocessor digital IC and a pacing analog IC can be integrated into a single IC while maintaining different operating voltages for the digital portion and the analog portion.

In some examples, a microprocessor in an IMD can be run at a lower voltage and frequency for general sensing, pacing, or monitoring activities, and the voltage or frequency can be increased for higher resource requirements such as therapy (e.g., defibrillation capacitor charging), communication (e.g., wireless telemetry), or arrhythmia detection or discrimination. This can significantly reduce the "on" time of a high voltage regulator and a high frequency oscillator, thereby reducing power consumption.

In some examples, an island of digital logic can be gated "off" (e.g., clock source disabled) to reduce the power consumption and thereby decrease the static current drain but still maintain sequential logic (e.g., maintain memory content). This may decrease the leakage current by orders of magnitude without compromising the function provided by the electronic circuits.

Figure 7:
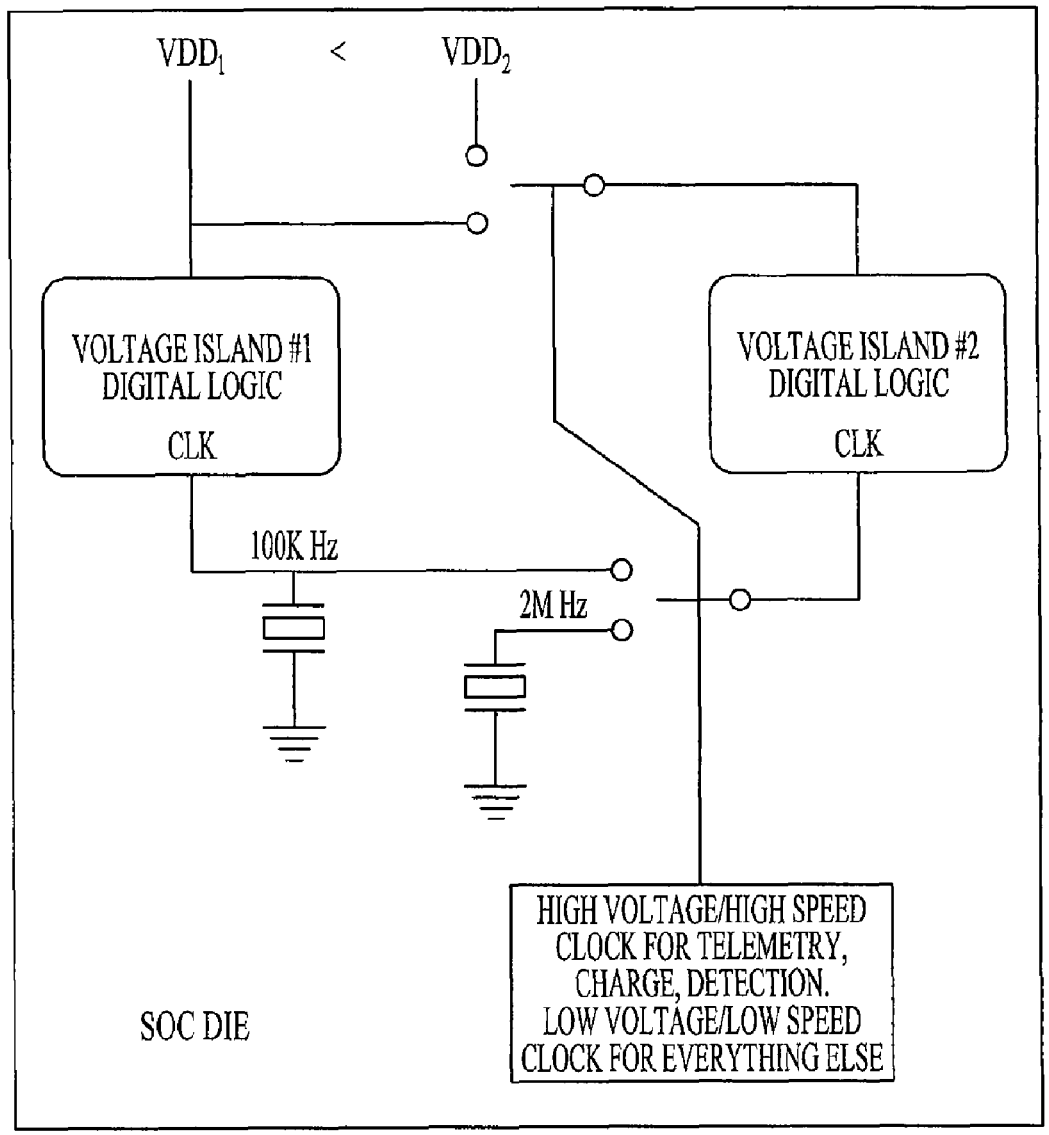
FIG. 7 shows an example of an IC with multiple voltage islands.

FIG. 7 shows an example of an IC with multiple voltage islands. FIG. 7 depicts a "digital-switching" of the supply from VDD1 to VDD2, which provides a different supply voltage level than VDD1. Another example can include only one VDD supply, which can be supplied by a power converter, and its supply voltage value can be controlled by another circuit or function. In this case, the VDD level can be changed in an analog (e.g., a continuous) fashion. This implementation can reduce the system complexity, such as by using only one off-chip decoupling capacitor for a supply, and by removing transient voltage spikes from the system by avoiding abrupt digital-like switching between different supply voltage values.

Static current drain can be reduced by disabling one or more voltage islands.

Figure 8:
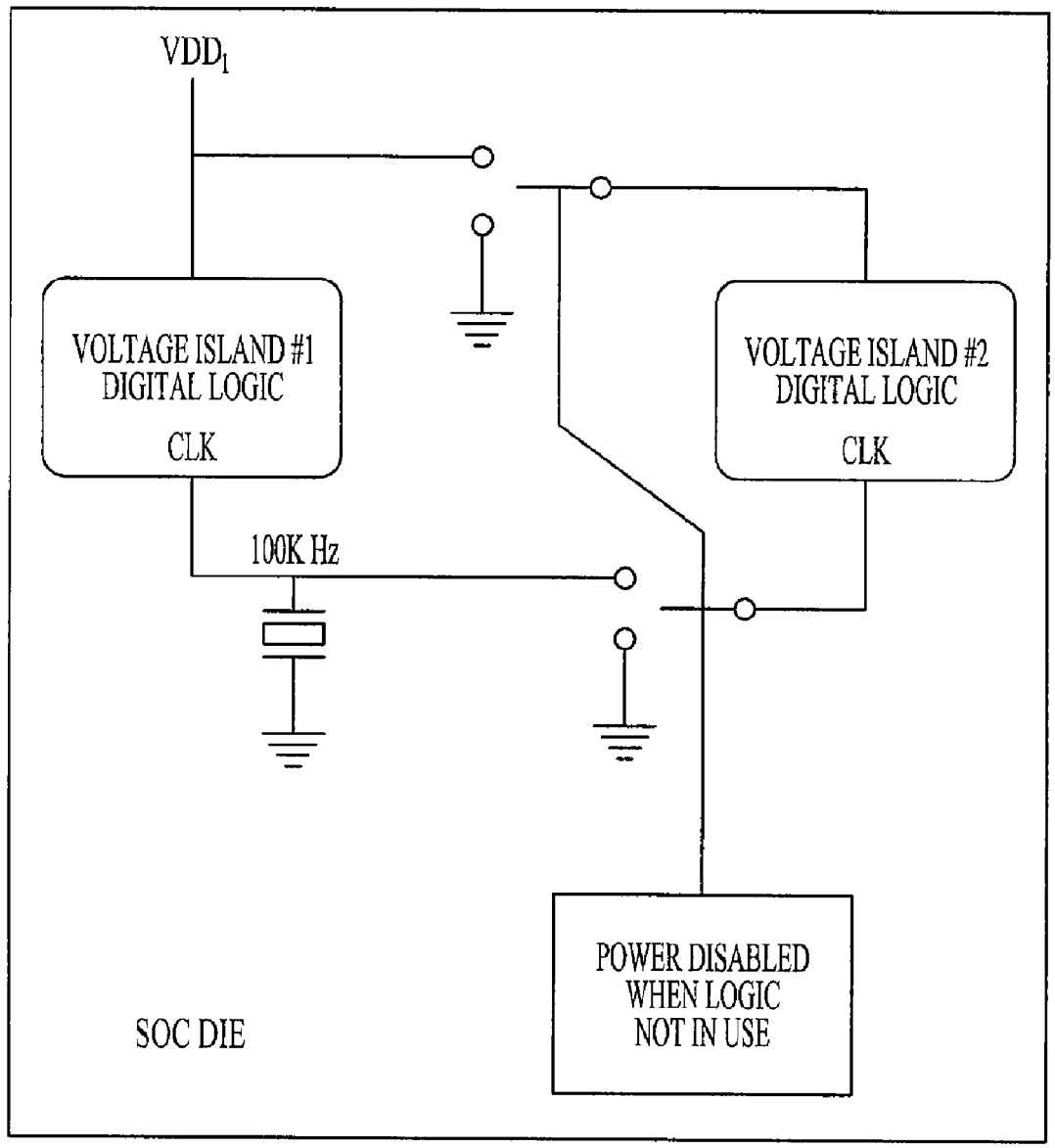
FIG. 8 shows an example of an IC that disables voltage islands.

Disabling voltage islands can be accomplished in certain examples by placing a switch on the VDD supply to a group of digital logic. An example of this is shown in FIG. 8. This is an aggressive method of reducing static current drain, but it also loses the sequential state of the design. Outputs of the disabled voltage island can be properly terminated to logic that remains powered. Note that the switch in series with the supply and logic can be sized such that it can handle the large dynamic current of all the gates it serves. This can involve a very large series switch, which can actually contribute significantly to the leakage current. When such a series switch is on, it can add a resistive drop, which further reduces the effective supply level (and therefore performance), as well as adding power supply noise, which can be dependent on the combinational loading.

IMD designs that include static random access memory (SRAM) can benefit from reducing power used by the SRAM. When using deep submicron technology, designs with SRAM have performance-to-power tradeoffs similar to those tradeoffs involved in logic design.

In IMD applications, the SRAM can be kept in an idle mode for most of the time. SRAM leakage current can be reduced by dynamically reducing the power supply for the SRAM during those periods of time while the SRAM is idle. The power supply can be reduced to a value as low as possible without losing the stored SRAM information contents. Such a minimum power supply level can be referred to as the Data Retention Value (DRV). In some examples, the power supply reduction is performed on one or more particular memory blocks of the memory, such that large amounts of memory can be controlled by one command or signal from a microprocessor. The DRV can be established at a value that includes enough margin to ensure data integrity for process and environmental effects (e.g., such as temperature variations or cosmic rays). The power supply reduction can be implemented using fixed supply values (e.g., active vs. idle) or adaptive supply values that can track one or more process or temperature conditions.

In some examples, the SRAM power supply can be turned off when the SRAM is not being used. For IMD subsystems that are used infrequently (e.g., a telemetry subsystem) and that use a large amount of scratch pad RAM, turning off the SRAM will remove a leakage path.

The present inventors have recognized that when choosing an SRAM cell for an IMD design, a trade off exists between leakage current and susceptibility to memory disruption events. An SRAM cell can be formed using a 6 transistor structure, which is sometimes referred to as the 6T structure. It can include a four-transistor latch and two transistors for read or write. Because of the number of transistors, a disadvantage of the 6T structure is the leakage current associated with the 6 transistors. Other cell structures can use fewer transistors, such as the one transistor structure (1T). However, the 1T uses a storage capacitor. Because of this, the 1T structure provides dynamic, not static, memory. The data, which is stored as a charge on the storage capacitor, leaks off the capacitor. Refresh cycles are used to maintain the data.

Also, the 1T structure uses a low-leakage capacitor that can be larger than the 6T structure, and may require a very specific process or additional process steps. The 6T structure can be desirable for IMD designs due to its static nature and its probable increased resistance to disruptions such as single-event upsets (SEUs). Leakage current of the 6T structure can be addressed, such as by using one or more of the techniques discussed above.

In contrast to the disadvantages of increased errors and increased static leakage current, deep submicron designs offer several opportunities recognized by the present inventors. One advantage is the capability to distribute IMD computational power.

In typical non-deep submicron designs, the size of a microprocessor was a significant amount of the overall digital area of an IC. With smaller geometry sizes, having multiple microprocessors on the same die not only becomes possible, but may have significant advantages in an IMD. The advantages of multiple microprocessors include the ability to concurrently process information in more than one microprocessor. For example, digital signal processing may be offloaded from a main microprocessor on a deep submicron IC to a second microprocessor on the same IC, wherein the second microprocessor can be fully powered-up only when such digital signal processing is needed. Also, smaller tasks can be offloaded from a main microprocessor to a second microprocessor on the same IC, wherein the second microprocessor can be configured with a reduced instruction set or otherwise scaled to the particular features or needs of the smaller task.

Another advantage recognized by the present inventors is the ability to decouple functions or features of an IMD from both a hardware and firmware perspective. With respect to hardware, this can significantly reduce circuit interactions from a myriad of system-on-chip (SOC) or analog/digital integration issues (such as supply coupling, substrate noise, EMI, etc.). This also allows for design development by function, or "canned" development.

Further advantages of multiple microprocessors recognized by the present inventors include the ability to support multiple firmware languages, the ability to segment the firmware of the device, such as to reduce validation or verification time, and to reduce bus congestion or bus widths to memories or other resources.

Another advantage of using deep submicron technology recognized by the present inventors is that it allows use of Field Programmable Gate Arrays (FPGAs) in IMD designs. In the past, use of FPGAs in IMDs was impractical due to size and power concerns. With smaller geometries, and VDD switching techniques described by the present inventors above, those limitations to using FPGAs may no longer exist. Use of FPGAs allows reconfigurable digital hardware, allowing new features to be implemented via the FPGA logic-even after implantation of the IMD.

Another advantage obtainable using deep submicron technology recognized by the present inventors is that smaller filler cells can be implemented to fill empty IC space. In some examples, normally empty (or wasted) IC space can be populated with logic with inputs or outputs that are tied off. The smaller geometry of devices of deep submicron technology allows more normally empty space to be filled with the logic cells. This places additional logic gates throughout the design that can be leveraged with a metal-only design change. These logic cells allow modification of an IC with a logic patch provided by one or more of the filler cell logic elements. Decoupling capacitors can also be placed in or used as filler cells in the empty space. The change can be implemented by modifying contact, the closest metal layer, or higher metal layers to patch the logic, such as to comply with an engineering change order.

A further advantage obtainable using deep submicron technology recognized by the present inventors is that, with the smaller geometries, reduced area can be traded off for increased flexibility, or vice-versa. For example, a finite state machine can be implemented with a programmable memory (e.g., a contact programmable ROM, EEPROM or Flash memory) instead of using combinational logic. The present inventors have recognized that this offers the advantage of being able to modify the state machine without doing an "all layer revision". Examples of IMDs that can implement device states in memory are found in Yost et al., U.S. Published Patent Application No. 20060247708, filed Apr. 28, 2005, which is incorporated herein in its entirety.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
an implantable medical device including a storage circuit comprising:
    a first stage configured to receive an input signal and including a first latch circuit having cross coupled logic gates configured to invert and store a data bit received in the input signal;
    a second stage circuit coupled to an output of the first stage circuit and including a second latch circuit having cross coupled logic gates configured to invert and store a data bit received from the first latch circuit;
    a clock circuit configured to receive a global clock signal and an off signal, and to provide a local clock signal to the first stage and second stage circuits, wherein the local clock signal is disabled when the off signal is received; and an error circuit coupled to the output of the first stage circuit and an output of the second stage circuit, wherein the error circuit is configured to generate an error indication when the outputs provide matching data bits while the off signal is active.

2. The apparatus of claim 1, wherein the second stage circuit is configured to store data on an opposite level of the global clock signal from the first stage circuit.

3. The apparatus of claim 1, wherein the storage circuit includes a first transistor that is wider than a second transistor of the storage circuit.

4. The apparatus of claim 1, wherein the implantable medical device comprises a cardiac function management device.

5. The apparatus of claim 1, wherein the implantable medical device comprises at least one of a neural stimulation device, a drug delivery device, or a diagnostic device.

6. An apparatus comprising:
an implantable medical device including a plurality of storage circuits, each storage circuit comprising:
a first stage circuit configured to receive an input signal and to invert and store a data bit received in the input signal;
a second stage circuit coupled to an output of the first stage circuit to invert and store a data bit received from the first stage circuit;
an error circuit coupled to the output of the first stage circuit and an output of the second stage circuit, wherein the error circuit is configured to generate an error indication when the storage circuit outputs provide matching data bits while the first stage circuit and the second stage circuit are in an inactive state, and wherein the error circuits are serially connected to form an error indication chain.

7. An apparatus comprising:
an implantable medical device including a storage circuit comprising:
a first stage circuit configured to receive an input signal and to invert and store a data bit received in the input signal;
a second stage circuit coupled to an output of the first stage circuit to invert and store a data bit received from the first stage circuit; and
an error circuit coupled to the output of the first stage circuit and an output of the second stage circuit, wherein the error circuit is configured to generate an error indication when the storage circuit outputs provide matching data bits while the first stage circuit and the second stage circuit are in an inactive state, wherein the storage circuit includes a first transistor having a voltage threshold that is lower than a voltage threshold of a second transistor of the storage circuit.

8. The apparatus of claim 7, wherein the first transistor is included in a signal path that is more time sensitive than a signal path including the second transistor.

9. The apparatus of claim 7, wherein the implantable medical device includes:
a logic gate circuit including a stack of three series connected transistors, wherein the three series connected transistors includes a first transistor having a voltage threshold that is lower than a voltage threshold of at least one of the other two transistors in the stack; and
wherein a gate of the first transistor is configured to receive an off signal to place the first transistor, the first stage storage circuit, and the second stage storage circuit in an inactive state.

10. An apparatus comprising:
an implantable medical device including:
a storage circuit comprising:
a first stage circuit configured to receive an input signal and to invert and store a data bit received in the input signal;
a second stage circuit coupled to an output of the first stage circuit to invert and store a data bit received from the first stage circuit; and
an error circuit coupled to the output of the first stage circuit and an output of the second stage circuit, wherein the error circuit is configured to generate an error indication when the storage circuit outputs provide matching data bits while the first stage circuit and the second stage circuit are in an inactive state; and
a redundancy circuit comprising:
first, second, and third logic circuits, wherein the second and third logic circuits are redundant instantiations of the first logic circuit; and
a voting circuit configured to determine an output of the redundancy circuit according to a majority of outputs of the first, second, and third logic circuits.

11. A method comprising:
receiving, at a clock circuit of an implantable medical device, a global clock signal and an off signal;
providing a local clock signal to a storage circuit of the implantable medical device;
storing information to represent an inverted version of a data bit in a latch circuit of a first stage of the storage circuit and storing a non-inverted version of the data bit in a latch circuit of a second stage of the storage circuit;
disabling the local clock signal when the off signal is received; and
generating an error indication when the stored information to represent the inverted and non-inverted versions of the data bit match while the off signal is active.

12. A method comprising:
storing, in a storage circuit of an implantable medical device, information to represent both an inverted version of a data bit and a non-inverted version of the data bit;
disabling clocking of the storage circuit;
generating an error indication when the stored information to represent the inverted and non-inverted versions of the data bit match while the clocking is disabled;
identifying a time sensitive signal path in the implantable device, wherein the time sensitive path includes the storage circuit; and
providing a first transistor having a voltage threshold that is lower than a voltage threshold of a second transistor, wherein the first transistor is included in the time critical signal path of the storage circuit, and wherein the second transistor is not included in the time critical signal path of the storage circuit.

13. A method comprising:
storing, in a storage circuit of an implantable medical device, information to represent both an inverted version of a data bit and a non-inverted version of the data bit;
disabling clocking of the storage circuit;
generating an error indication when the stored information to represent the inverted and non-inverted versions of the data bit match while the clocking is disabled;
providing a logic gate circuit that includes three series connected transistors, and wherein the three series connected transistors includes a first transistor having a voltage threshold lower than the voltage threshold of at least one of the other two transistors; and disabling the first transistor when disabling the clocking of the storage circuit.

14. A method comprising:
storing, in a storage circuit of an implantable medical device, information to represent both an inverted version of a data bit and a non-inverted version of the data bit;
disabling clocking of the storage circuit;
generating an error indication when the stored information to represent the inverted and non-inverted versions of the data bit match while the clocking is disabled;
generating first, second, and third logic outputs, wherein the second and third logic outputs are generated using logic that is redundant to logic used to generate the first and second logic outputs; and
voting using the first, second, and third logic outputs to determine a majority output.

15. A method comprising:
providing a clock signal to a storage circuit of an implantable medical device;
storing, in the storage circuit, information to represent both an inverted version of a data bit and a non-inverted version of the data bit, wherein the inverted version of the data bit is stored on an opposite level of the clock signal than the information to represent the non-inverted version of data bit;
disabling clocking of the storage circuit; and
generating an error indication when the stored information to represent the inverted and non-inverted versions of the data bit match while the clocking is disabled.

16. The method of claim 15, comprising using the error indication to detect a disruption to operation of a cardiac function management device.

17. The method of claim 15, comprising using the error indication to detect a disruption to operation of at least one of a neural stimulation device, a drug delivery device, or a diagnostic device.

18. A method comprising:
storing, in a storage circuit of an implantable medical device, information to represent both an inverted version of a data bit and a non-inverted version of the data bit;
disabling clocking of the storage circuit;
generating an error indication when the stored information to represent the inverted and non-inverted versions of the data bit match while the clocking is disabled;
providing a plurality of the storage circuits in association with respective error circuits;
serially connecting the error circuits of the storage circuits into an error chain; and
propagating an error indication to an output of the error chain when an error occurs in any of the storage circuits during disabling of the clocking of the storage circuits.

19. A method comprising:
storing, in a storage circuit of an implantable medical device, information to represent both an inverted version of a data bit and a non-inverted version of the data bit;
disabling clocking of the storage circuit;
generating an error indication when the stored information to represent the inverted and non-inverted versions of the data bit match while the clocking is disabled; and
rewriting a register that includes a plurality of the storage circuits when an error indication is generated.

* * * * *